(12) United States Patent
Smith

(10) Patent No.: US 11,944,779 B2
(45) Date of Patent: Apr. 2, 2024

(54) INTRAVENOUS FLUID BAG SUPPORTING ASSEMBLY

(71) Applicant: Walter L. Smith, Glen Allen, VA (US)

(72) Inventor: Walter L. Smith, Glen Allen, VA (US)

( * ) Notice: Subject to any disclaimer, the term of this patent is extended or adjusted under 35 U.S.C. 154(b) by 233 days.

(21) Appl. No.: 17/073,743

(22) Filed: Oct. 19, 2020

(65) Prior Publication Data

US 2022/0118175 A1 Apr. 21, 2022

(51) Int. Cl.
*A61M 5/14* (2006.01)

(52) U.S. Cl.
CPC ........ *A61M 5/1417* (2013.01); *A61M 5/1415* (2013.01); *A61M 5/1418* (2013.01); *A61M 2205/587* (2013.01); *A61M 2209/082* (2013.01); *A61M 2209/084* (2013.01)

(58) Field of Classification Search
CPC .... A61M 5/1413–1415; A61M 5/1417; A61M 2205/587; A61M 2209/084; A61M 2209/082; A61G 7/0503; A47B 57/42; A47B 57/56; A47B 2220/0008; A45B 3/02
USPC ....................................... 211/85.13; D24/128
See application file for complete search history.

(56) References Cited

U.S. PATENT DOCUMENTS

| | | | | |
|---|---|---|---|---|
| 3,460,789 A | * | 8/1969 | Engelsher | A61M 5/1415 248/318 |
| 3,552,577 A | * | 1/1971 | Latham | A61B 50/10 211/74 |
| 3,653,617 A | * | 4/1972 | Saternus | A61M 5/1415 248/278.1 |
| 4,332,378 A | * | 6/1982 | Pryor | A61M 5/1415 211/205 |
| D269,121 S | * | 5/1983 | Pollard | D24/128 |
| 4,706,368 A | * | 11/1987 | Crissman, III | A61M 5/1415 29/525.09 |
| 4,756,706 A | * | 7/1988 | Kerns | A61M 5/142 128/DIG. 13 |
| 4,898,578 A | * | 2/1990 | Rubalcaba, Jr. | A61M 5/172 700/83 |
| 5,114,023 A | * | 5/1992 | Lavin | A47B 57/54 D24/128 |
| 5,421,548 A | | 6/1995 | Bennett et al. | |

(Continued)

FOREIGN PATENT DOCUMENTS

| | | |
|---|---|---|
| CN | 102657905 A | 9/2012 |
| JP | 2003310712 A | 11/2003 |

(Continued)

*Primary Examiner* — Ingrid M Weinhold
(74) *Attorney, Agent, or Firm* — LEADING-EDGE LAW GROUP

(57) ABSTRACT

An intravenous fluid bag supporting assembly includes a mobile base having a plurality of wheels, a telescoping pole having a lower end connected with the base and an inverted polyhedron structure connected with an upper end of the pole and configured to receive at least one intravenous fluid bag. An adjustable light assembly is arranged on the pole in spaced relation between the inverted polyhedron structure and the base. A support platform is arranged on the pole in spaced relation between the light assembly and the base, the support platform supporting a plurality of housings configured to receive a plurality of displays and pumps or other medical instruments, respectively. A hang grip and basket are also arranged on the pole.

18 Claims, 18 Drawing Sheets

(56) References Cited

U.S. PATENT DOCUMENTS

| | | | | |
|---|---|---|---|---|
| 5,876,371 | A * | 3/1999 | Yokoyama | A61M 5/1413 604/80 |
| 6,250,482 | B1 * | 6/2001 | Want | A61M 1/61 5/503.1 |
| 6,407,335 | B1 | 6/2002 | Franklin-Lees et al. | |
| D497,447 | S * | 10/2004 | Yoneda | D26/24 |
| 6,969,031 | B2 | 11/2005 | Ugent et al. | |
| D540,485 | S * | 4/2007 | Waedeled | D26/70 |
| 7,213,951 | B2 * | 5/2007 | Cowan | A47B 87/0246 362/406 |
| D558,908 | S * | 1/2008 | Waedeled | D26/67 |
| D568,467 | S | 5/2008 | Cottone | |
| 7,401,936 | B1 * | 7/2008 | Fan | A45B 3/04 362/102 |
| 7,533,854 | B2 * | 5/2009 | Aube | A61M 5/1417 248/95 |
| D627,063 | S | 11/2010 | West et al. | |
| 7,874,410 | B2 | 1/2011 | Fulbrook et al. | |
| 8,360,241 | B2 * | 1/2013 | Lu | A61M 5/1415 209/3.3 |
| 8,381,662 | B2 * | 2/2013 | Goldszer | A47B 37/04 135/16 |
| D680,673 | S * | 4/2013 | Levine | D26/60 |
| 9,284,968 | B2 * | 3/2016 | Clouser | F16B 2/14 |
| 9,511,185 | B2 * | 12/2016 | Slaker | A61M 5/1418 |
| 10,151,425 | B1 * | 12/2018 | Bileth | B25H 3/06 |
| 10,383,697 | B2 * | 8/2019 | Karasina | A61B 50/15 |
| 10,426,887 | B2 | 10/2019 | Koehler et al. | |
| D866,037 | S * | 11/2019 | Hu | D26/67 |
| 10,478,548 | B2 | 11/2019 | Blankenship et al. | |
| 2003/0106969 | A1 * | 6/2003 | Dillon | A61M 5/1415 248/129 |
| 2006/0278771 | A1 * | 12/2006 | Ho | A61G 7/1017 248/129 |
| 2007/0159772 | A1 | 7/2007 | Morice | |
| 2007/0267551 | A1 | 11/2007 | Townsend | |
| 2009/0261215 | A1 | 10/2009 | Lambert | |
| 2009/0294604 | A1 * | 12/2009 | Sunderland | F16M 11/42 248/227.3 |
| 2009/0301927 | A1 * | 12/2009 | Fvlbrook | A61B 90/57 248/304 |
| 2010/0052274 | A1 * | 3/2010 | West | A61M 5/1417 280/47.24 |
| 2012/0273445 | A1 * | 11/2012 | Cregg | B62B 3/12 211/85.8 |
| 2014/0209550 | A1 * | 7/2014 | Pryor | A61M 5/1417 211/85.13 |
| 2016/0114102 | A1 | 4/2016 | Yamamoto et al. | |
| 2017/0290633 | A1 | 10/2017 | Burke et al. | |
| 2018/0132966 | A1 | 5/2018 | Desaulniers et al. | |

FOREIGN PATENT DOCUMENTS

| | | |
|---|---|---|
| JP | 2014233398 A | 12/2014 |
| KR | 20180095963 | 2/2017 |

* cited by examiner

INTRAVENOUS FLUID BAG SUPPORTING ASSEMBLY

BACKGROUND OF THE DISCLOSURE

A conventional intravenous ("IV") fluid bag stand or pole has two components: a wheeled base for multidirectional movement and a hook assembly or attachment for receiving one or more intravenous fluid bags.

IV poles are designed to assist in uniform dosing of fluids at uniform rates but can be confusing for care givers and cumbersome for patients. For care givers, problems stem from potentially having four pumps attached to a single display, coupled with IV fluid bags hanging above the displays and pumps and arranged in no particular order. To add to the confusion, specific fluid lines must connect with specific access points in a patient. Care giver efficiency is lost when trying to ensure that the correct fluid lines are connected at the access points. To aid in this process, care givers often attach pieces of tape at the top and bottom of IV lines to identify which line is which. Furthermore, a single, central display with pumps on each side can be confusing to read, leading to dosing and dispensing errors.

In today's hospital environment, it is common for multiple medical devices, e.g., syringe pumps, infusion pumps, vital sign monitoring devices, etc., to be simultaneously used to treat and monitor an individual patient. In such situations, these instruments may also be affixed or arranged on an IV stand positioned near the patient. The number and arrangement of these devices can further contribute to delays in rapid identification, label reading errors and misidentification of IV fluid bags and corresponding medical devices.

For many patients, the IV pole is a necessary evil. Clinical evidence shows that patients who walk at least 45 minutes a day do better in recovery. Unfortunately, prior art IV poles are not friendly in this regard. Pumps are attached to the sides of the displays, and the displays are then attached to the pole, making the pole assembly unbalanced.

The mobility of patients is further inhibited when medical lines become caught in the IV pole wheels or become tangled and drag on the floor. In general, hospital personnel prefer to discard items that touch the floor.

IV stands frequently have bases arranged in a symmetrical star or spoked configuration with extensions that radiate from a center of the base. Patients walking with such poles find them awkward and unwieldy. Patient injury can also result from accidentally kicking or tripping over exposed wheels and spokes while walking along side such IV stand base configurations.

Conventionally IV stands include multiple hooks for mounting multiple medication bags for a patient. Some configurations include a plurality of hooks arranged in a circular or longitudinal pattern. In either of these configurations, there may be a set of bags arranged in front of other bags in which case, only the labels on the front bags may be viewed; labels on the rear bags are obscured by the front bags.

Additional drawbacks of these arrangements can be found in the directional orientation of the hooks. Health care providers may have difficulty mounting the bags on the hooks. Once hung, owing to the height of the hooks and bag arrangement, care givers have difficulty viewing the fluid bags and labels to identify the contents, particularly for patients requiring large numbers of contemporaneous transfusions. In other cases, the arrangement of the bags can obscure labels on other bags. To read the bags, medical personnel must reposition the bags. This can be difficult if the bags and associated fluid lines are attached to a patient. Furthermore, such arrangements may contribute to delays in rapid label identification, leading to label reading errors and misidentification of IV fluid bags.

When a central display is arranged on an IV stand, multiple pumps are arranged linearly on either side of the display. A first pump is attached to a left side of the display and is designated "pump A." When a second pump is added, to help maintain the balance of the IV pole, the second pump is arranged on a right side of the pump and designated "pump B." Confusion arises with the later addition of additional pumps. For example, when a third pump is added, to promote balance of the IV stand, the third pump will be arranged on a left side of "pump A." The linear arrangement is third pump, first pump, display, second pump. The addition of the third pump, however, changes the designation of all pumps. The third pump becomes "pump A," the second pump is redesignated "pump B," the second pump is redesignated "pump C." When a fourth pump is added to the IV stand, it is arranged to the right of the second pump and is designated "pump d." As a consequence of this naming and renaming convention employed by existing display/pump combinations, confusion results in identifying which IV fluid is associated with which pump/display designation. As previously indicated, care givers often attach pieces of tape at the top and bottom of IV lines to identify which line is which.

In addition, multiple lengths of flexible tubing extend from the IV fluid bags to the patient and may become crossed or entangled with one another, increasing the burden on medical personnel to distinguish one length of tubing from another when connecting the tubing to the fluid bags and to the patient and/or when injecting additional medications into the patient via tubing inlets. To assist medical personnel, colored coded tape is often employed to improve identification.

Because such arrangements lack uniformity in the distance spanned from any one hook to any one pump, IV fluid lines are excessively long. Freedom of patient movement can vary by several feet depending on where a fluid bag is hung on a rake and the location of a pump. Unnecessarily long IV fluid lines may become entangled in IV pole wheels, requiring a patient to push, lift or otherwise manipulate the IV stand to free the entangle line. To help prevent the excess fluid line length from becoming a hazard, fluid lines may be draped over or around a central pump, or even over the top of the fluid bag rake. Such actions lead to additional confusion as to the origin and destination of IV fluid lines.

A patient, while walking, can roll the IV stand along their side and within reach of one or more lengths of flexible tubing through which IV fluid flows from one or more medication bags to the patient. Mobile IV stands may not have a handle for a patient to comfortably grasp while walking. Patients often resort to using the top of a pump or other medical device as a handhold. Where handles are provided, they are not easily adjusted to a height comfortable for each individual user or may include a mounting configuration that is not easy for a patient to safely and comfortably grasp for stability while walking. Some handles place an undue strain on a user's hand and wrist resulting in discomfort and fatigue.

Once medical devices and collateral equipment and devices are properly secured to an IV stand, all electrified instruments must be connected to a power outlet. This results in a conglomeration of medical devices, a plurality of power cords and electronic wiring that leads to a tangled mass of cords and wires spread on a hospital room floor providing a source of contamination and infection spread. When relocating a patient, all power supply lines must be unplugged and are frequently hung over the top of the IV stand or coiled around medical devices. This is awkward and inefficient on the one hand. If the power lines touch the floor, to avoid infection, cords must be thoroughly cleaned prior to re-use.

SUMMARY OF THE DISCLOSURE

To improve the efficiency of medical personnel and to improve patient comfort, a compact, mobile IV pole assembly is provided in which all assembly elements are axially arranged.

The IV fluid bag supporting assembly includes a mobile base having a plurality of wheels, a telescoping pole having a lower end connected with the mobile base, and an inverted polyhedron structure connected to an upper end of the pole. The inverted polyhedron structure is configured to receive at least one IV fluid bag.

The IV fluid bag supporting assembly also includes a light assembly having angularly adjustable lights, a support platform configured for receiving a plurality of housings for IV pumps and displays, a hand grip or handle and a basket. All of these elements are axially arranged on the pole in spaced relation between the inverted polyhedron and the mobile base.

In use, medical personnel hang an IV fluid bag from one of the hooks arranged on a side surface of the inverted polyhedron structure.

An IV fluid line is attached to the bag and fed down the pole to the light assembly platform. A free end of the IV fluid line is fed first into a central through opening of the light assembly and then connected with a pump arranged in a support platform housing. From the pump, the IV fluid line is then fed into a central through opening of the support platform. Finally, the free end of the IV fluid line is connected with a patient.

By arranging the IV fluid lines within the through openings of the light assembly platform and support platform, IV fluid lines will hang directly below a corresponding IV fluid bag before being connected with a pump arranged in the support platform housing corresponding to a particular inverted polyhedron side surface. The arrangement of the polyhedron side surfaces, light assembly platform through opening, support platform housings and support platform through opening cooperate to reduce the likelihood that IV fluid lines will be misidentified or become tangled or ensnared. Such an arrangement will improve the ease with which medical personnel can correlate respective fluid bags, pumps and fluid lines.

Because all of the IV fluid bag supporting assembly elements are axially arranged, waste, sanitation and environmental concerns are improved. Axial arrangement of all assembly components establishes uniformity in the distance from the top if the inverted polyhedron structure to the underside of the support platform. The uniform distance allows utilization of shorter IV fluid lines because all assembly elements are arranged at approximately the same distance originating at the inverted polyhedron, down the telescoping pole, through the light assembly central through opening to housings arranged on the support platform. Similarly, axial arrangement of housings on the support platform supports uniformity in length of IV fluid lines extending from any given housing to a patient. Plastic waste is reduced.

BRIEF DESCRIPTION OF THE FIGURES

These and other aspects of the invention are described in more detail in the accompanying description when viewed in the light of the accompanying drawings, in which.

DETAILED DESCRIPTION

Figure 1:
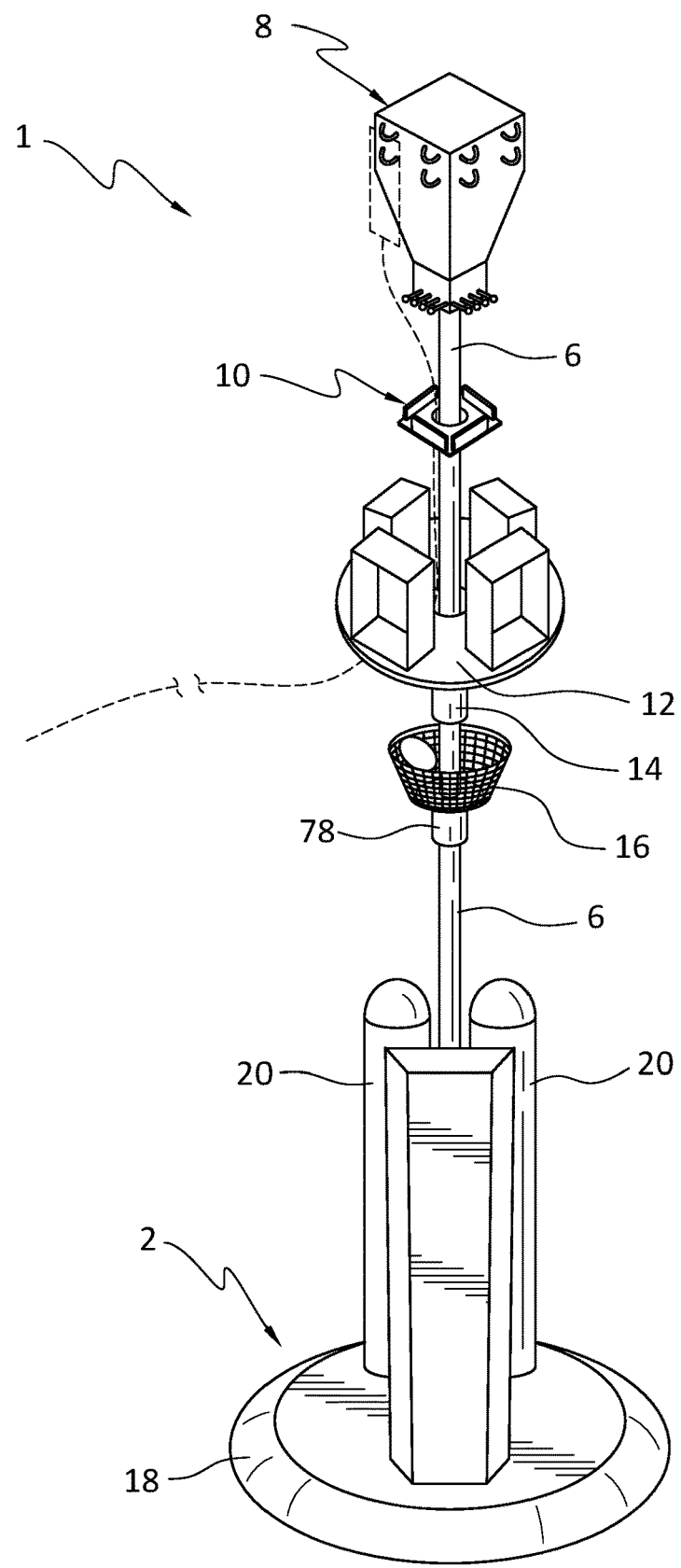
FIG. 1 is a perspective view of the IV stand according to the present disclosure.

The IV fluid bag supporting assembly 1 of FIG. 1 includes a mobile base 2 having a plurality of wheels 4, a telescoping pole 6 having a lower end connected with the mobile base 2, and an inverted polyhedron structure 8 connected with an upper end of the pole 6. The inverted polyhedron structure 8 is configured to receive at least one IV fluid bag. The IV fluid bag support assembly 1 also includes a light assembly 10, a support platform 12, a hand grip or handle 14 and a basket 16.

Figure 2:
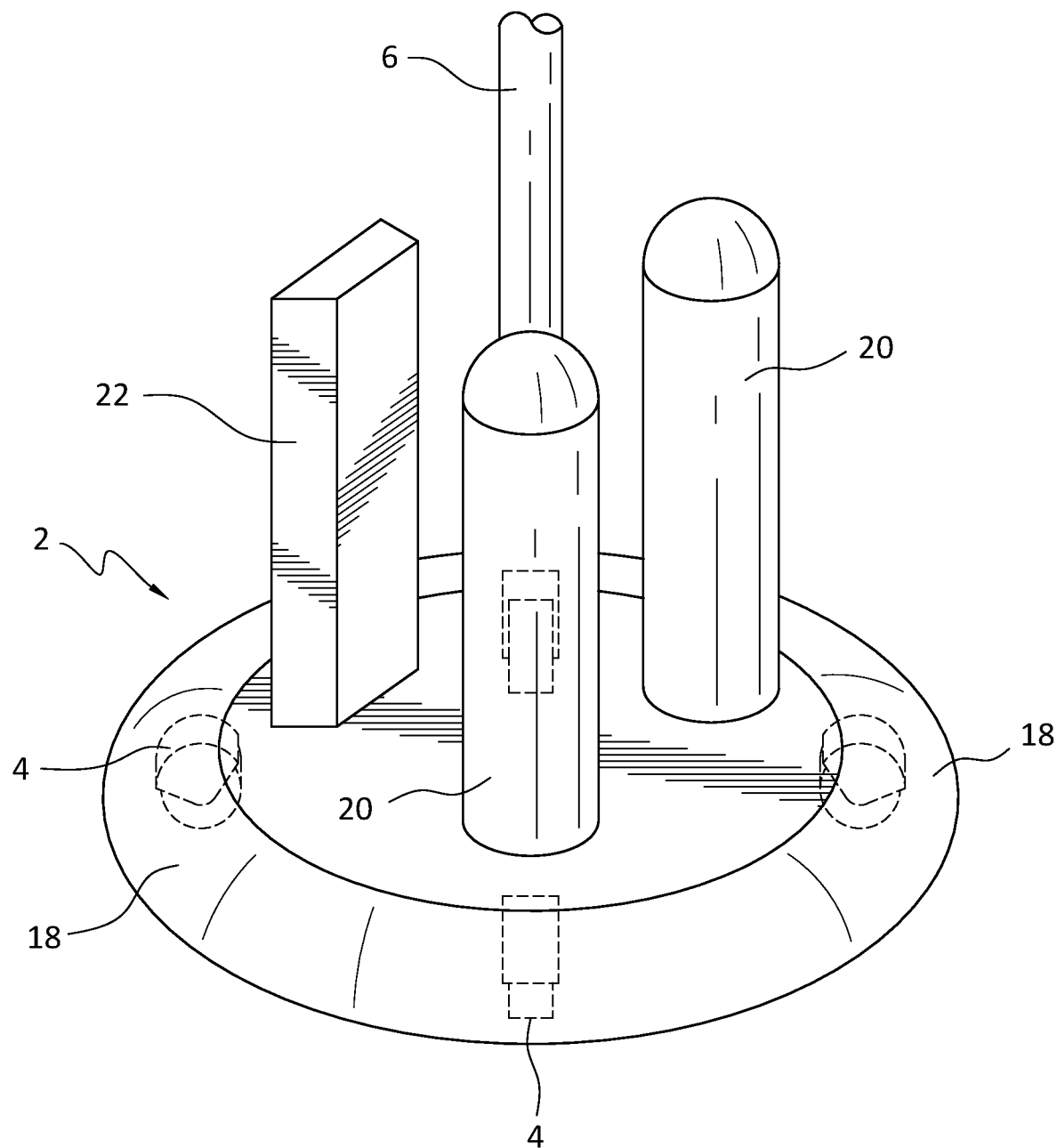
FIG. 2 is an enlarged perspective view of the mobile base according to FIG. 1 with the wheel skirt partially removed.

As illustrated in FIG. 2, the wheels 4 of the mobile base 2 may be casters, encased ball bearing wheels or any other suitable wheel assembly. The mobile base 2 may be encircled by a wheel cover or skirt 18 as shown in FIG. 1. In an example, the wheel cover 18 may be fixed, hinged, removable or connected with the base by any other suitable arrangement.

The mobile base 2 may be sized and configured to receive at least one of an oxygen tank 20, a power outlet strip or bar 22 and other equipment arranged axially around the pole. In an embodiment, the power outlet strip 22 may include a retractable power cable.

To reduce injury to a patient from tripping over or knocking ankles against the mobile base, the diameter of the mobile base is reduced to a minimum. To compensate for the reduced diameter and improve stability of the IV fluid bag assembly 1, a mass of the mobile base 2 is greater than a mass of the inverted polyhedron structure 8. The mass of the mobile base 2 will provide stability to the assembly and help prevent the IV fluid bag assembly 1 from tipping over when traveling over bumpy terrain or across thresholds.

A telescoping pole 6 is connected to the mobile base 2 at a lower end of the pole. In an example the pole 6 may be adjustable. The pole 6 may be hollow and have an interior diameter sized for receiving a plurality of electrical lines for powering on board electronics. The pole 6 may also include one or more hooks, holders or other devices for receiving and removably securing a free end of a power cable or other article.

The telescoping pole 6 may include fastening devices (not illustrated) for securing one or more oxygen tanks 20 arranged on the mobile base 2 to the IV fluid pole assembly 1.

An inverted polyhedron structure 8 is arranged at a top end of the pole 6. Side surfaces 24 of the inverted polyhedron structure 8 are configured to receive a plurality of hooks 26 from which a plurality of IV fluid bags are suspended. Optionally, side surfaces 24 of the inverted polyhedron structure 8 are configured to receive a plurality of hangers 28 for receiving cap strips and other items frequently used by medical personnel.

Figure 3:
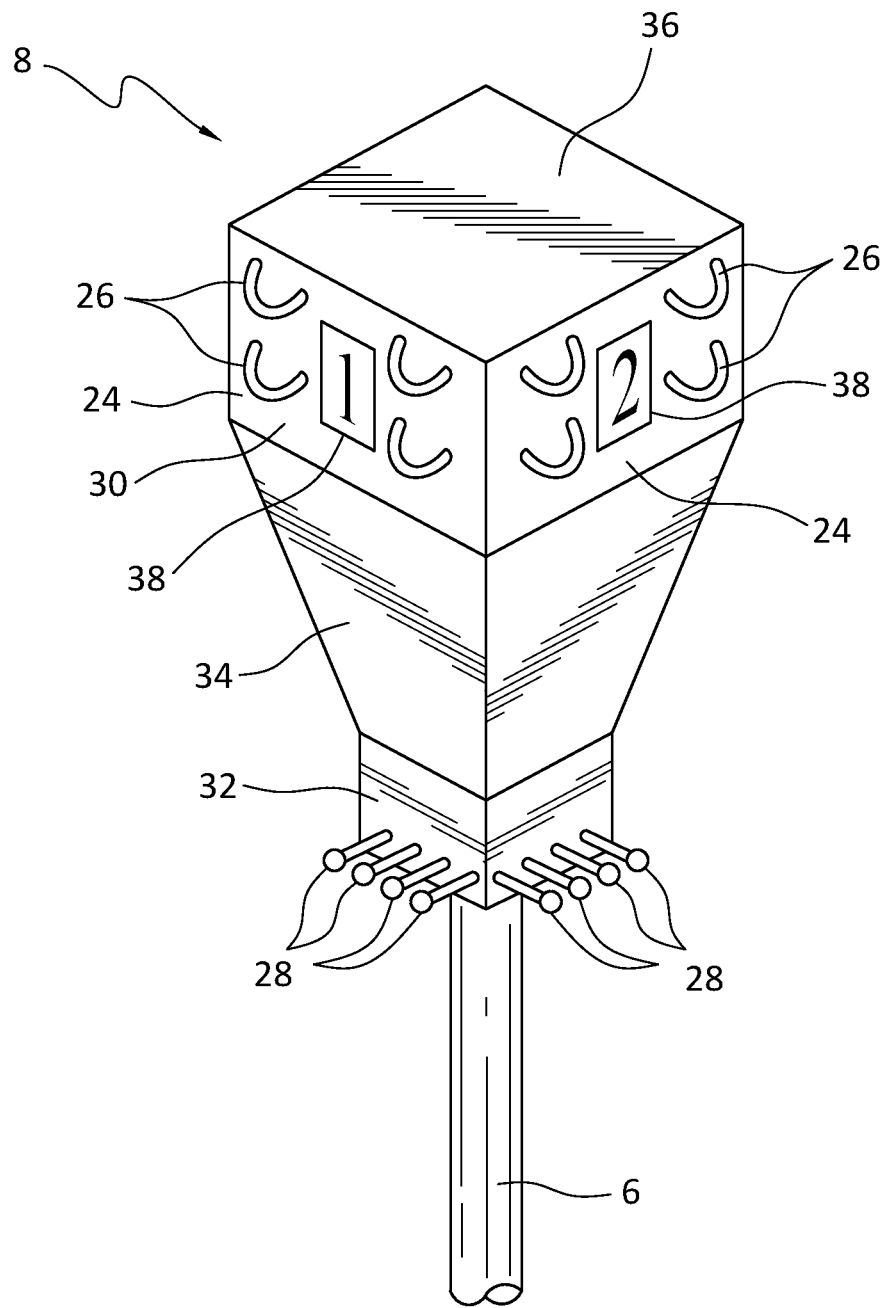
FIG. 3 is an enlarged perspective view of the inverted polyhedron structure arranged at one end of the IV stand according to FIG. 1.
Figure 4:
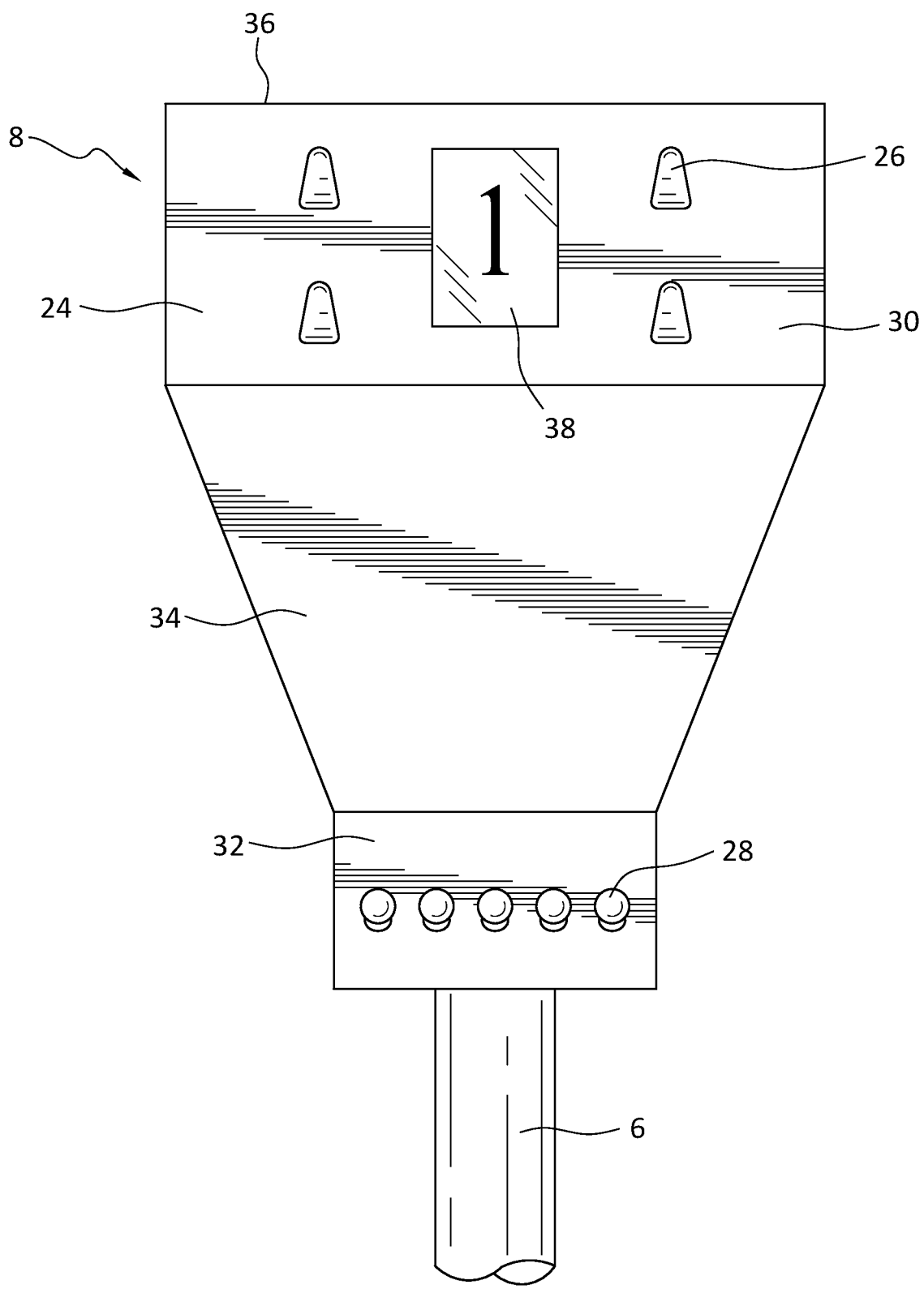
FIG. 4 is a plan view of a side surface of the inverted polyhedron structure of FIG. 3.
Figure 5:
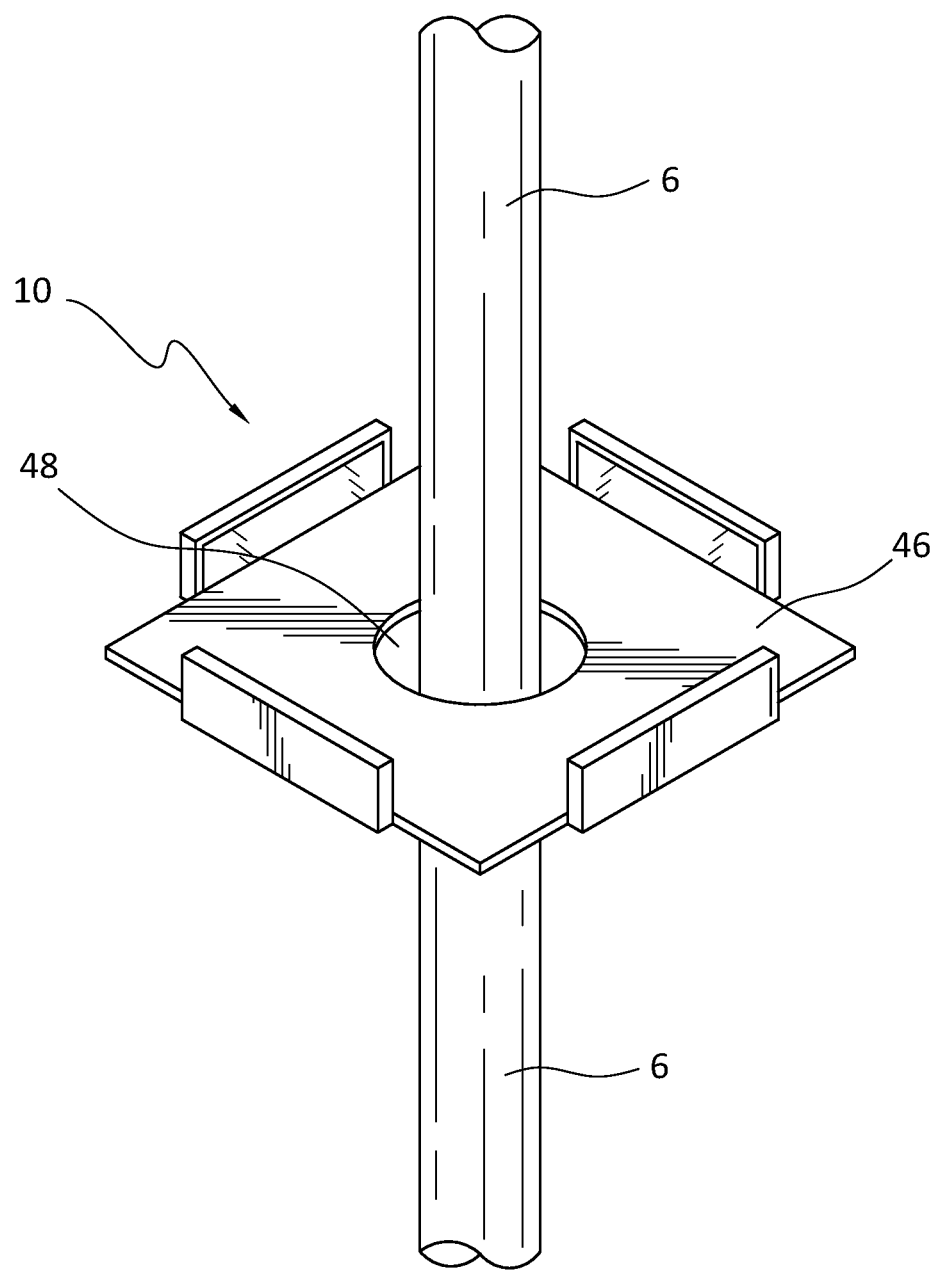
FIG. 5 is an enlarged view of the light assembly of FIG. 1.
Figure 6:
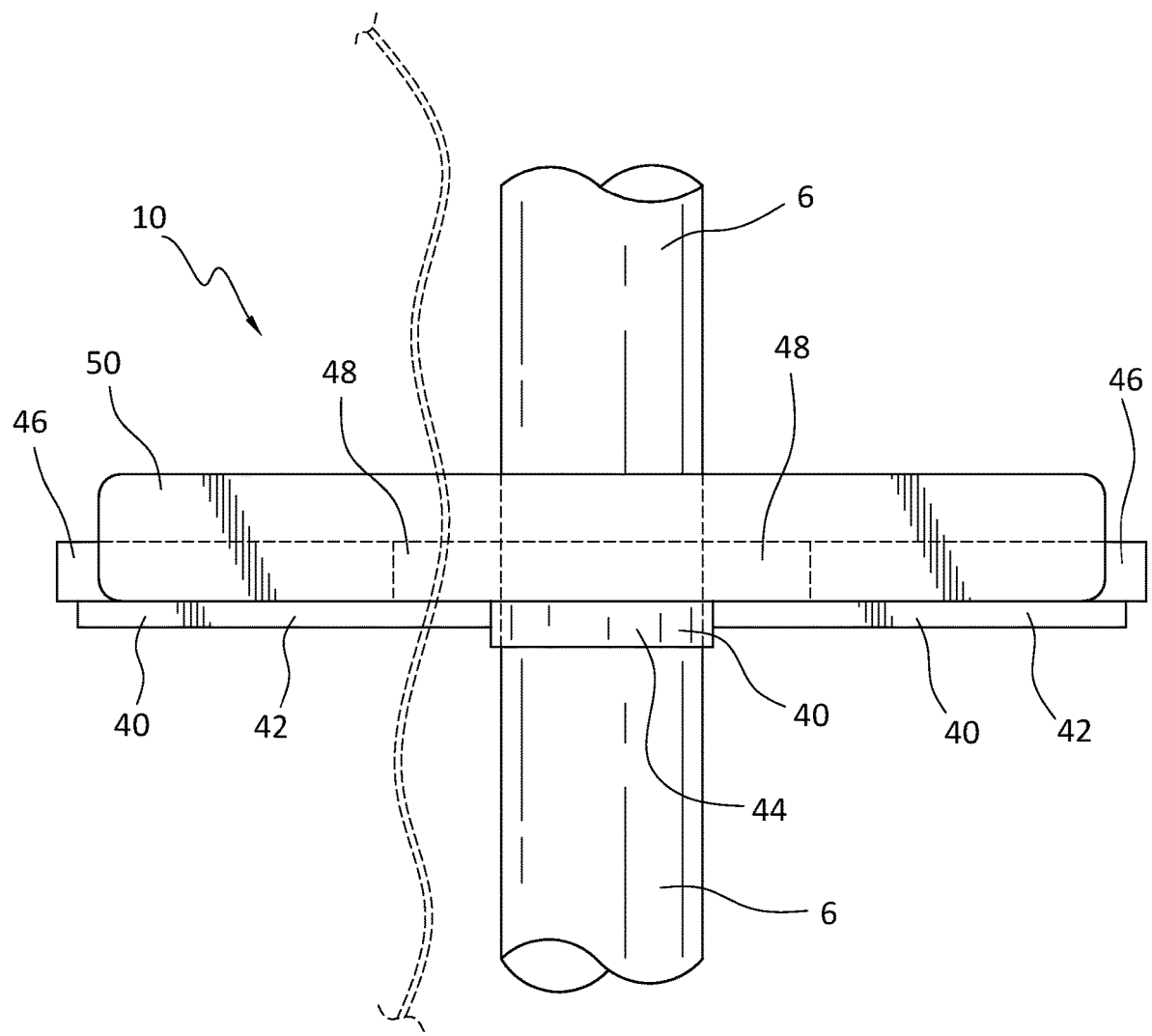
FIG. 6 is a plan view of a side surface of the light assembly of FIG. 5.
Figure 7:
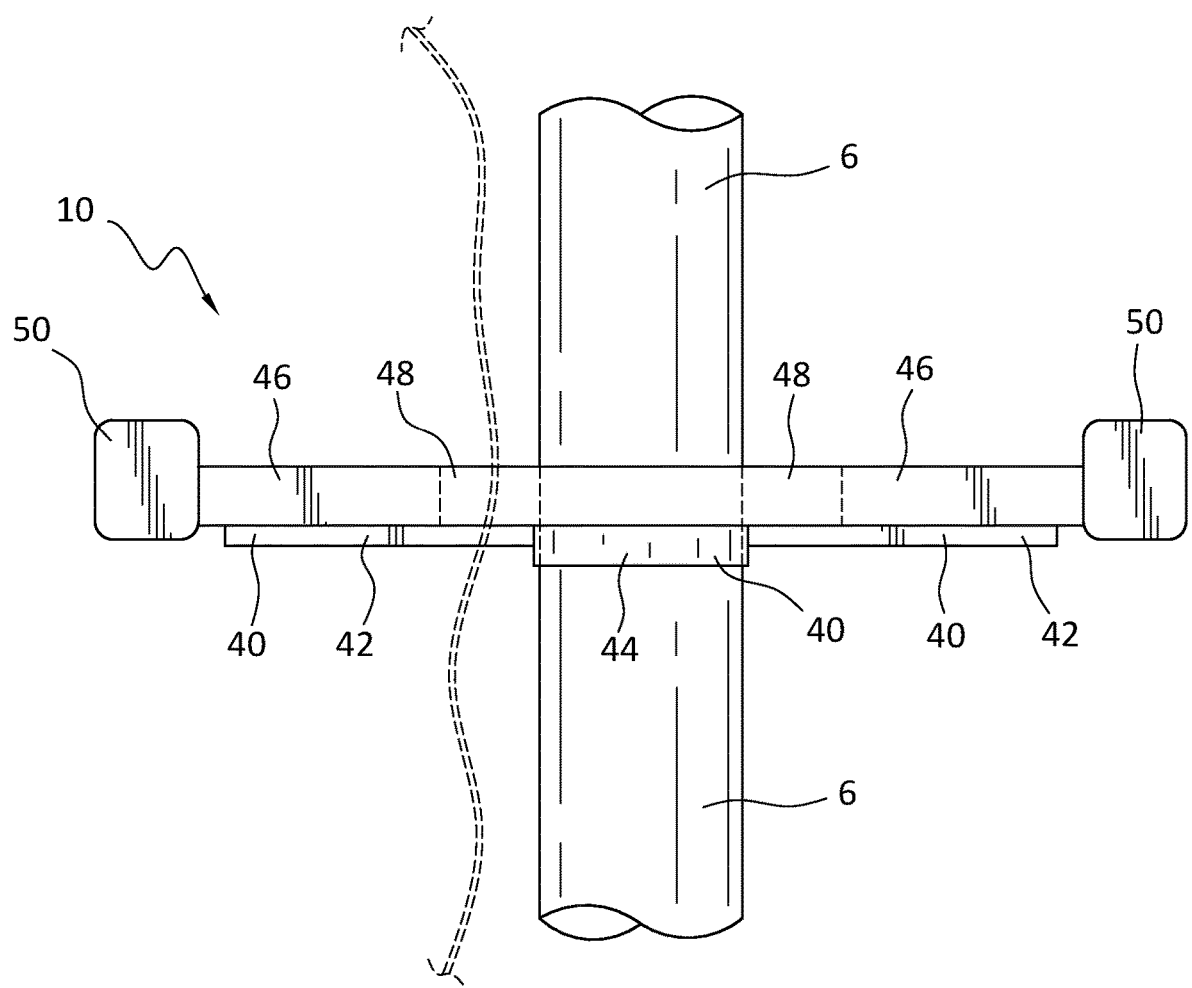
FIG. 7 is an alternative plan view of a side surface of the light assembly of FIG. 5.
Figure 8:
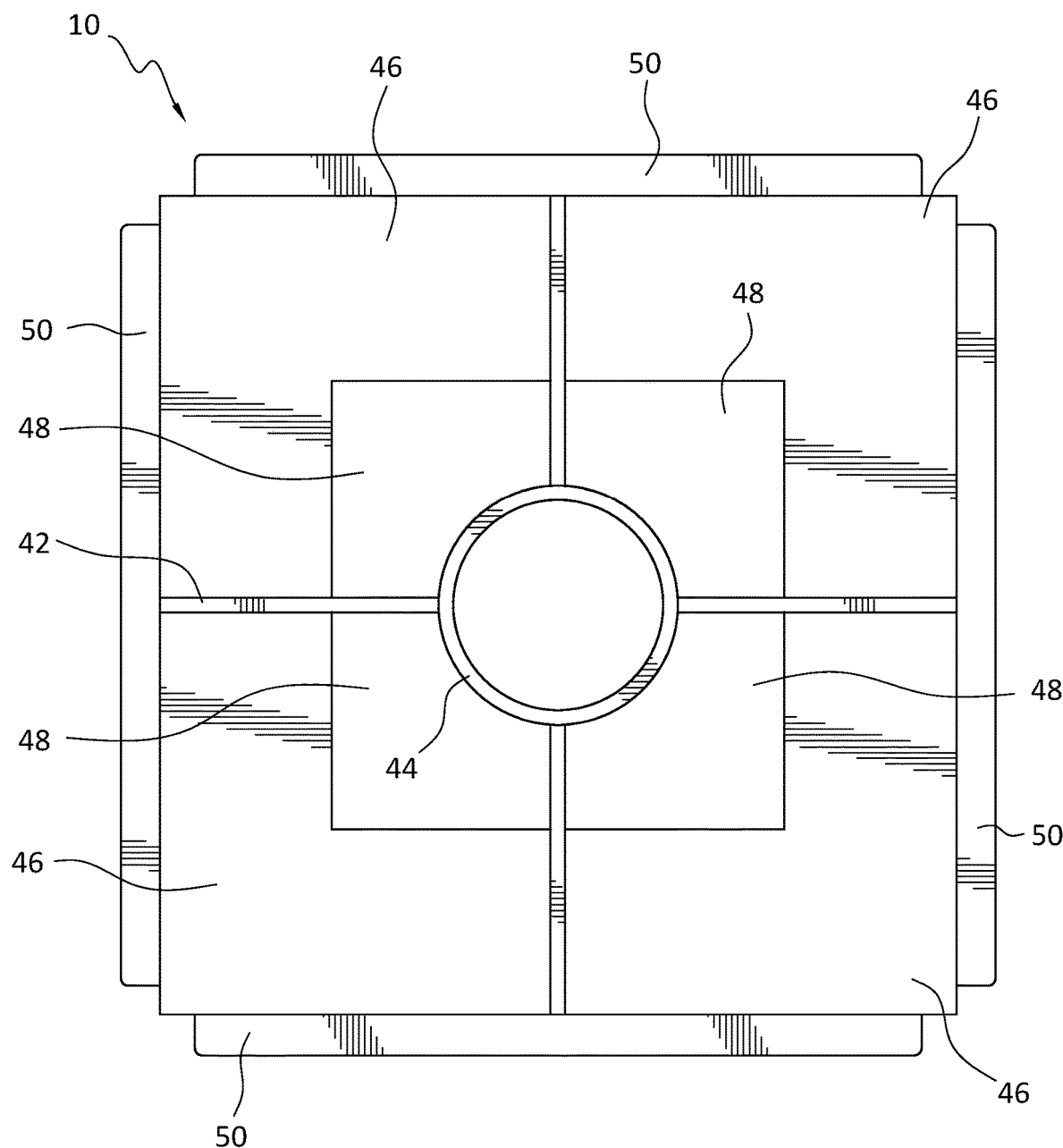
FIG. 8 is a bottom plan view of the light assembly of FIG. 5 in a first configuration.
Figure 9:
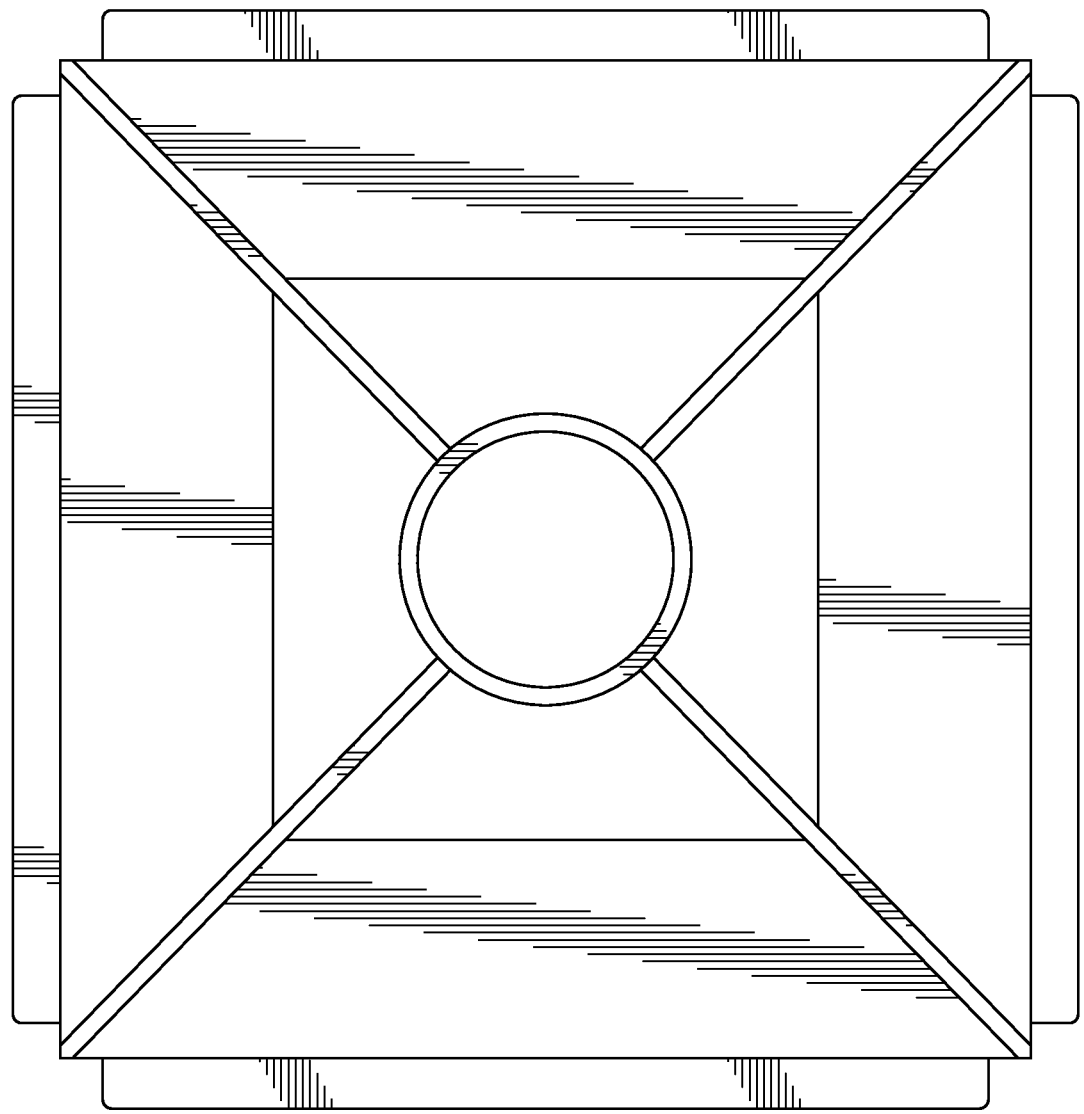
FIG. 9 is a bottom plan view of the light assembly of FIG. 5 in a second configuration.

As illustrated in FIGS. 1 and 3, the inverted polyhedron structure 8 includes a generally rectangular top portion 30 that tapers downwardly to a generally square bottom portion 32. A perimeter of the top portion 30 is greater than a perimeter of the bottom portion 32. Intermediate side surface portions 34 of the inverted polyhedron 8 are angled inward so that when IV fluid bags hang from hooks 26, the angled side surfaces 34 permit an upper portion of an IV fluid bag to touch a side surface 24 of the inverted polyhedron structure 8 while a lower portion of the IV fluid bag hangs away from the inverted polyhedron structure 8. The inverted structure allows the bags to hang unencumbered while helping to keep labels affixed to the bags oriented for more ready viewing and identification.

A plurality of hooks 26 may be arranged on side surfaces 24 of the top portion 30 of the inverted polyhedron structure 8. The hooks 26 may be configured to receive a plurality of IV fluid bags and may be arranged such that an outermost extension of a hook 26 is arranged at approximately the same height as a top surface 36 of the inverted polyhedron structure 8. In an example, the polyhedron structure 8 may be configured to receive sixteen IV fluid bags.

A plurality of hangers 28 may be arranged on the lower portion 32 of the polyhedron structure 8. The hangers 28 may be beaded knobs or other structures suitable for receiving and hanging cap strips or other items for the convenience of medical personnel.

In an embodiment, the inverted polyhedron structure 8 includes indicia 38 for distinguishing each side surface from other side surfaces. The indicia 38 may be at least one of a color, number and icon.

As illustrated in FIGS. 1, and 5-12, a light assembly 10 may be arranged on the pole 6 in spaced relation between the base 2 and the inverted polyhedron structure 8. In an alternative configuration (not illustrated), the light assembly may be arranged above the polyhedron structure.

The light assembly may be supported on the pole by a collared strut arrangement 40, the collared strut arrangement 40 having a plurality of struts 42 radiating from a collar 44. The number and arrangement of the struts 42 may vary according to the material composition of the collared strut arrangement 40 in relation to the mass of the light assembly 10. The collar 44 may be attached to the pole 6 by any known device.

The light assembly platform or support structure 46 may be arranged on top of the collared strut arrangement 40 and may include a central through opening 48 to receive the pole 8 and at least one IV fluid line. Preferably, the light assembly platform 46 through opening 48 is configured to receive the pole and a plurality of IV fluid lines.

The light assembly platform 46 may be further configured for receiving a plurality of angularly adjustable lights 50. A perimeter of the light assembly platform 46 may have a configuration corresponding with the inverted polyhedron structure 8. The number of lights 50 arranged on the light assembly platform 46 may correspond to the number of side surfaces 24 of the inverted polyhedron structure 8.

Electrical lines for powering the light assembly 10 may be arranged inside the pole 6.

The arrangement and wattage of the angularly adjustable lights 50 may be selected for patient consideration. To aid medical personnel in viewing IV fluid bags or associated pumps, displays and other medical devices that may be attached to the IV pole 6, the plurality of angularly adjustable lights 50 may be arranged on the light assembly platform 46 so that the lights shine upward or downward on the IV pole assembly and are focused so as to not illuminate a darkened room and disturb a resting or sleeping patient. Only one of the plurality of lights may be illuminated at any given time. Alternatively, a plurality of the lights may be simultaneously illuminated.

Figure 10:
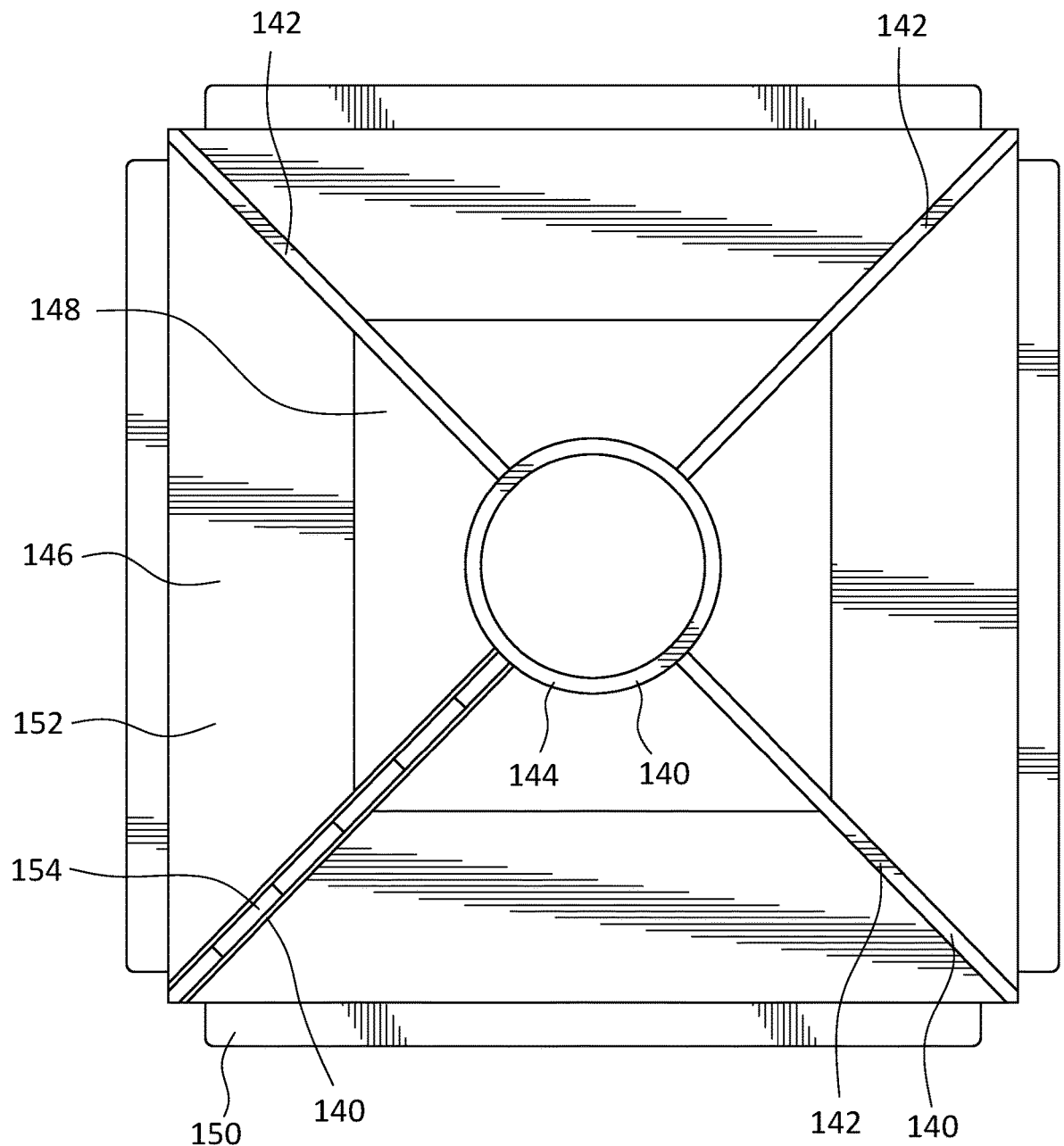
FIG. 10 is a bottom plan view of the light assembly of FIG. 5 in a third configuration.

In the alternative configuration of FIG. 10, the light assembly platform 146 may be segmented, with at least one segment 152 being connected with the strut arrangement 140 by one or more hinges 154. In this configuration, when a hinged segment of the light assembly platform is lifted, medical personnel gain easier access to the light platform central through opening 148, thereby aiding in the addition or removal of IV fluid lines from the central through opening 148. This embodiment also includes struts 142 and angularly adjustable lights 150 as with the embodiment of FIG. 8.

Figure 11:
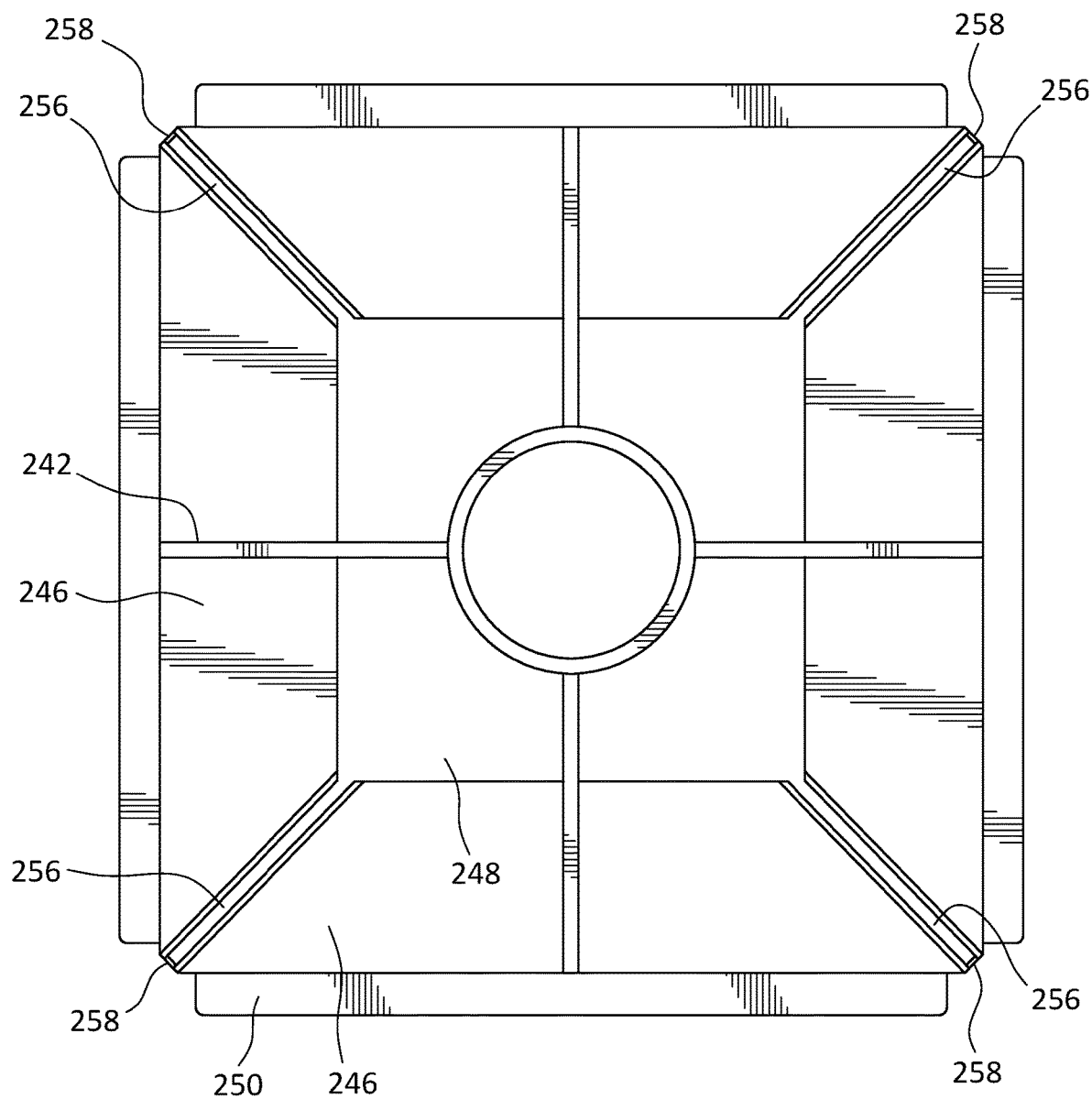
FIG. 11 is a bottom plan view of the light assembly of FIG. 5 in a fourth configuration.

In the alternative configuration of FIG. 11, the light assembly platform 246 may be segmented by one or more slots 256 extending from an outer edge portion of the light assembly platform to the central through opening 248. In this configuration, the slot may optionally be closed by a gate 258. To assist medical personnel with the addition of an IV fluid line to the light assembly platform central through opening 248, the optional gate 258 may be opened, and an IV fluid line may be fed from outside the perimeter of the segmented platform, through slot 256 into the central through opening 248. To remove an IV fluid line from the light assembly platform through opening 248, the reverse procedure is followed. This embodiment also includes struts 242 and angularly adjustable lights 250 as with the embodiment of FIG. 8.

Figure 12:
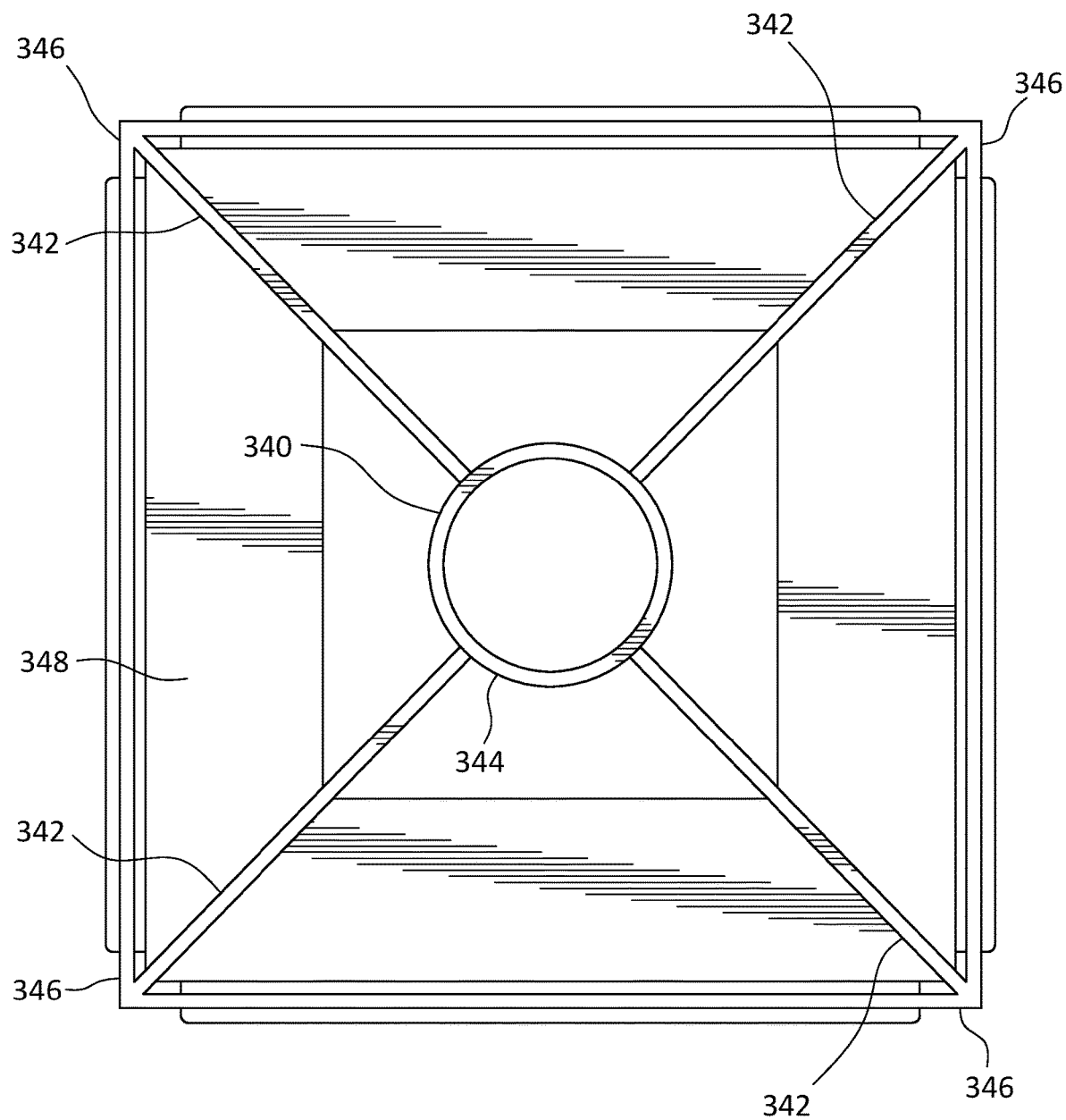
FIG. 12 is a bottom plan view of the light assembly of FIG. 5 in a fifth configuration.

In the alternative configuration of FIG. 12, the angularly adjustable lights may be arranged around a perimeter of a light assembly support structure connected to the collared strut arrangement 340. In an example, the support structure may be a frame 346 wherein an area surrounded by a frame element 346 and a strut 342 and the support collar 344 is open 348 and configured for receiving at least one IV fluid line.

As illustrated in FIGS. 1 and 13-18, the IV fluid bag support assembly 1 further includes a support platform 12 having a central through opening 60 sized for receiving the pole 6 and a plurality of IV fluid lines. The support platform 12 may be arranged on the pole 6 in spaced relation between the light assembly 10 and the mobile base 2 and may be supported on the pole 6 by a collared strut arrangement 62. The number and arrangement of the struts 64 may vary according to the material composition of the collared strut arrangement 62 in relation to the mass of the support assembly 12 under load. The collar 66 may be attached to the pole 6 by any known device.

Figure 17:
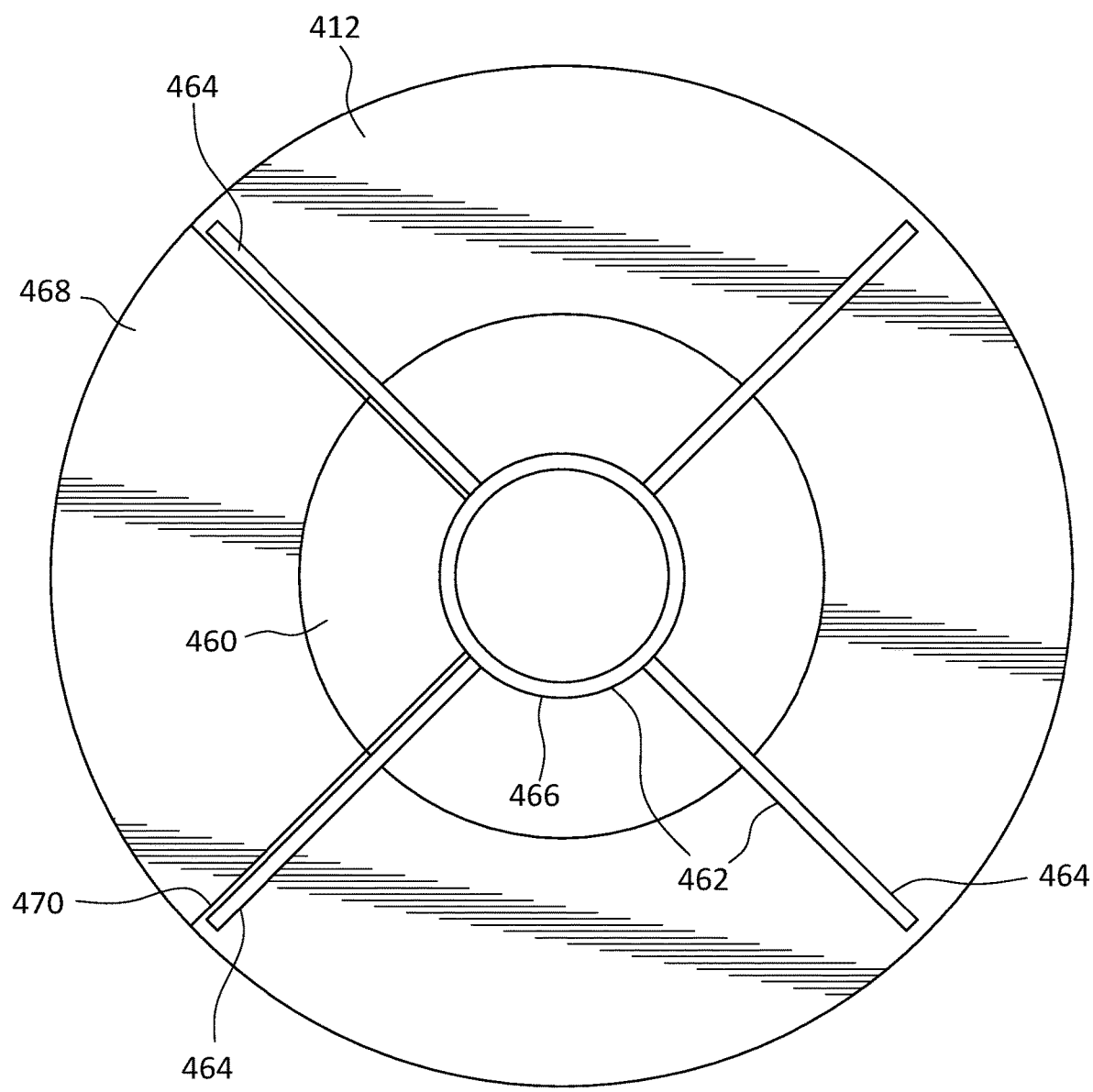
FIG. 17 is a bottom view of the support platform of FIG. 13 in a second configuration.

In the alternative configuration of FIG. 17, the support platform 412 may be segmented, with at least one segment 468 being connected with the strut arrangement 462 by one or more hinges 470. In this configuration, when a hinged segment of the support assembly platform is lifted, medical personnel gain easier access to the support platform central through opening 460, thereby aiding in the addition or removal of IV fluid lines from the central through opening 460. This embodiment also includes struts 464 and a collar 466 as with the embodiment of FIG. 14.

Figure 18:
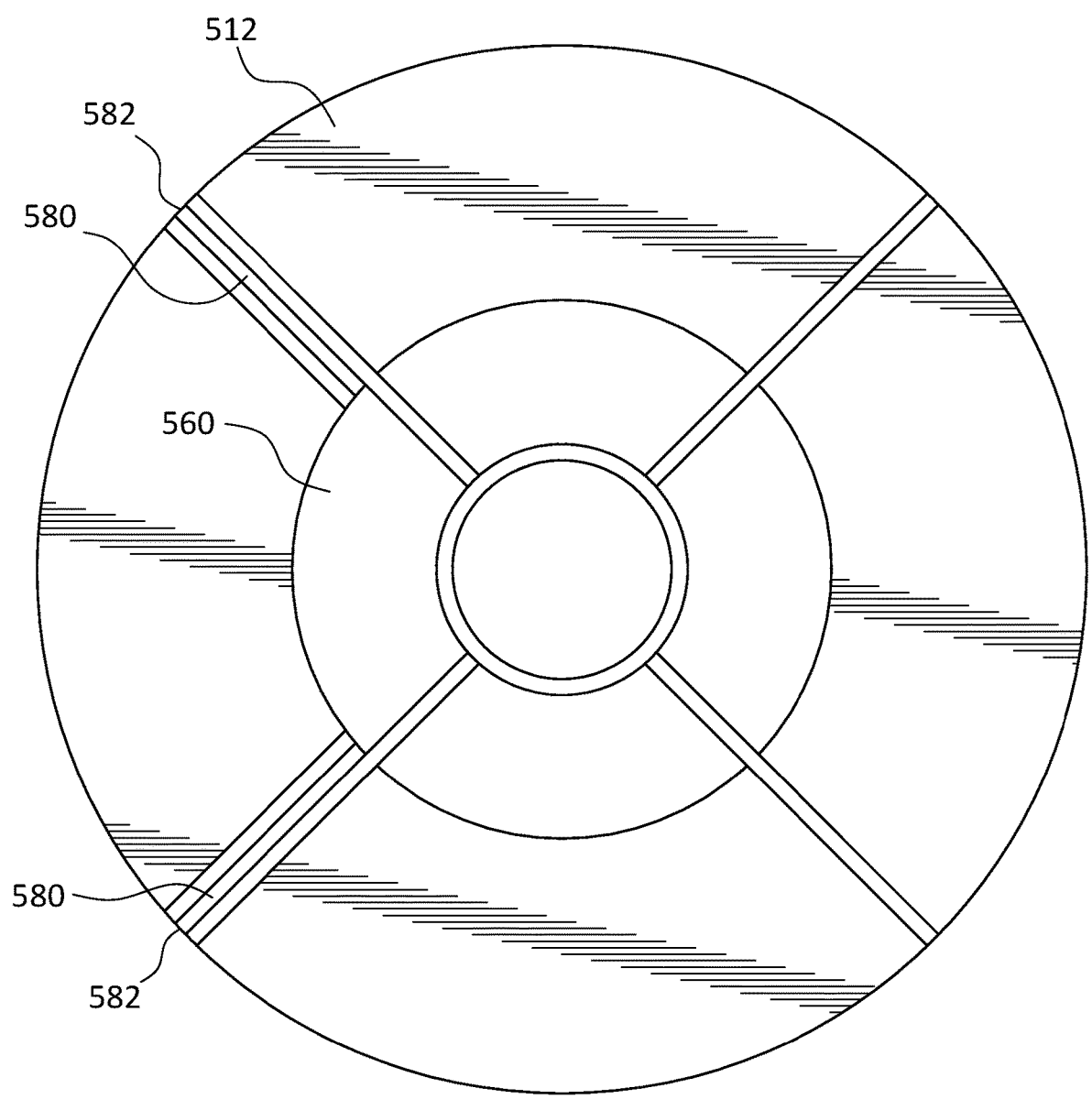
FIG. 18 is a bottom view of the support platform of FIG. 13 in a third configuration.

In the alternative configuration of FIG. 18, the support platform 512 may be segmented by one or more slots 580 extending from an outer edge portion of the support platform to the central through opening 560. In this configuration, the slot may optionally be closed by a gate 582. To assist medical personnel with the addition of an IV fluid line to the support platform central through opening 5600, the optional gate 582 may be opened, and an IV fluid line may be fed from outside the perimeter of the segmented platform, through a slot into the central through opening. To remove an IV fluid line from the support platform through opening, the reverse procedure is followed.

The support platform 12 may be configured to receive a plurality of housings 72 for displays, pumps or other medical devices and instruments. In an example, the number of housings 72 corresponds with the number of side surfaces 24 on the inverted polyhedron structure 8.

In an example, the indicia 38 represented on a particular side surface 24 of the inverted polyhedron structure 8 will have corresponding indicia 73 designated on at least one housing 72 wall. In practice, medical personnel will associate indicia 38 on the inverted polyhedron structure 8 with a particular IV fluid bag and display or pump housing 72 having corresponding indicia 73. To further aid in identification, medical personnel may attach corresponding indicia to a particular IV fluid line. Use of indicia will reduce time spent by medical personnel tracing an IV fluid bag and line to a particular device as well as help reduce misidentification errors.

Sterility maintenance is a concern to medical personnel. If IV fluid bags or lines contact floor surfaces, these items are discarded as a matter of course. If an IV line is temporarily disconnected from a patient, medical personnel will attach a cap to a free end of a fluid line. To assist medical personnel with keeping free ends of capped lines associated with specific IV bags and pumps, the support platform of FIGS. 14-15 may optionally include a plurality of notches 74 each for receiving a free end of a capped fluid line. A width of a notch 74 is greater than a diameter of a fluid line and smaller than a diameter of a fluid line cap. In use, a capped line is inserted into a notch. Once the capped line is released by medical personnel, the cap will rest on an upper surface of the support platform and the IV fluid line will hang below the support platform. Because the support platform 12 is arranged above the floor, tubing will not touch the floor or become ensnared in the mobile base.

Electrical lines for powering medical devices or instruments inserted into the housings may be arranged inside the pole.

Figure 13:
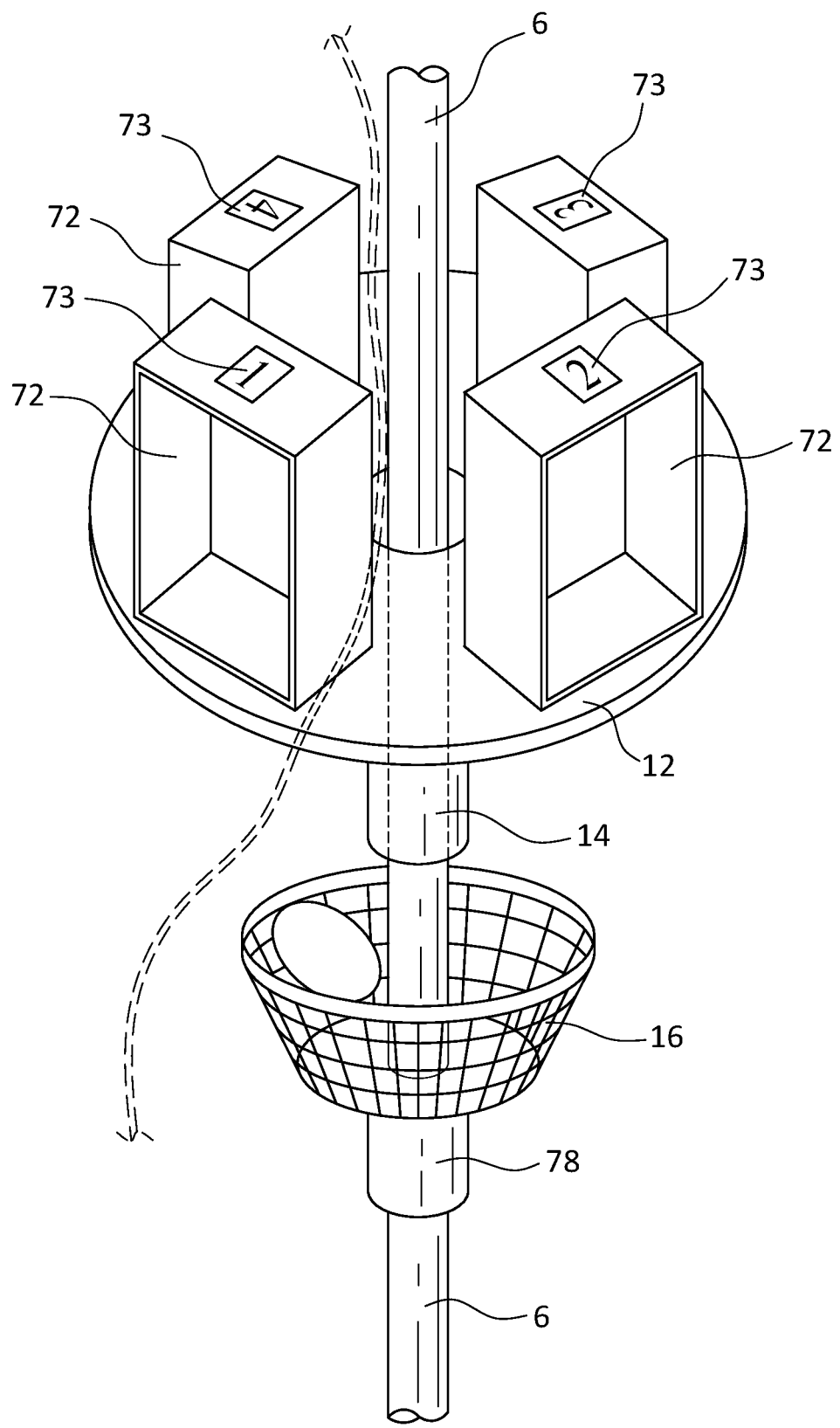
FIG. 13 is an enlarged perspective view of the support platform, hand grip and storage basket of FIG. 1.
Figure 14:
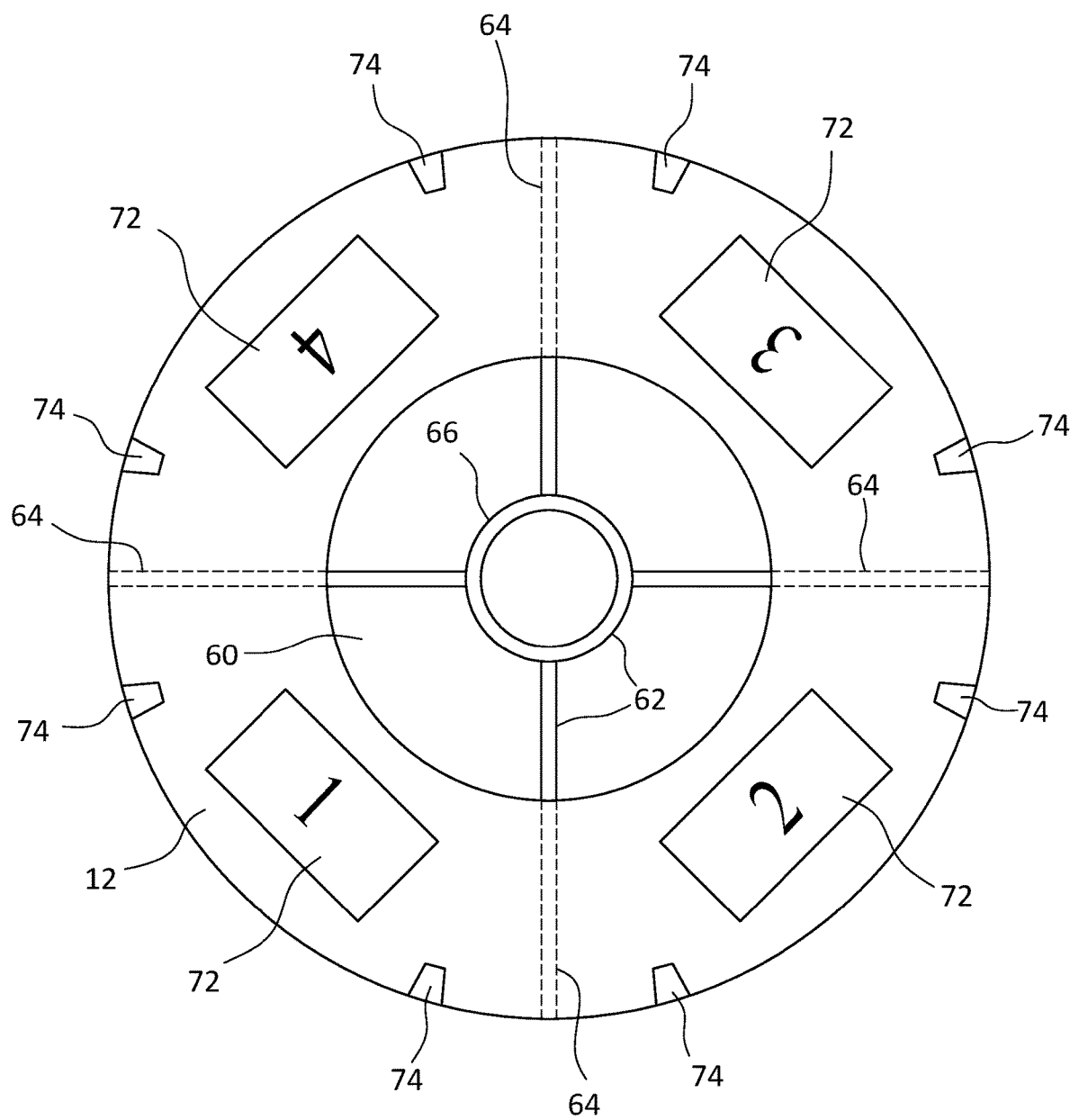
FIG. 14 is a top view of the support platform of FIG. 13.
Figure 15:
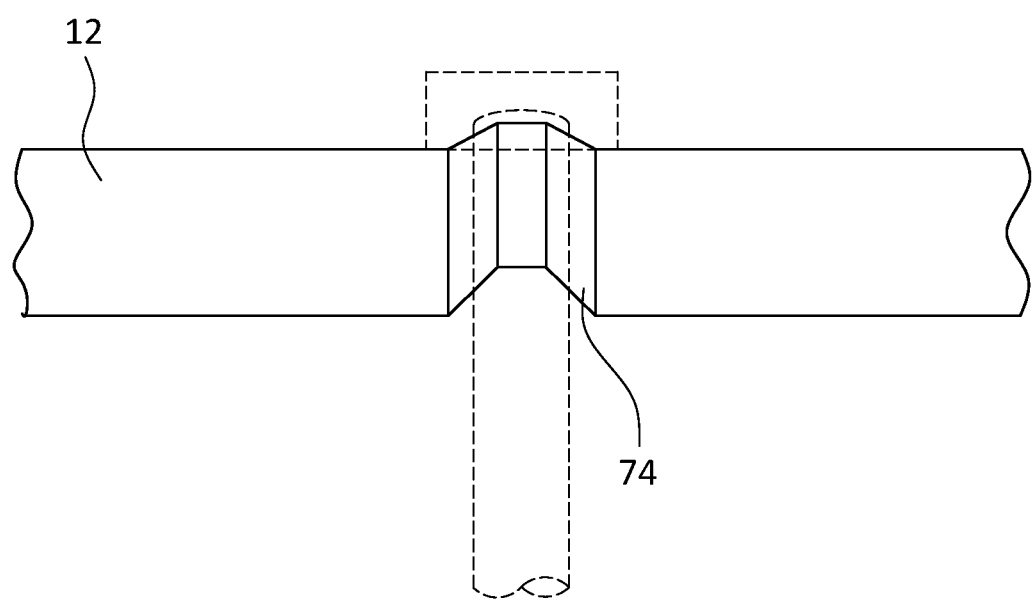
FIG. 15 is an enlarged partial side view of the support platform of FIG. 13.
Figure 16:
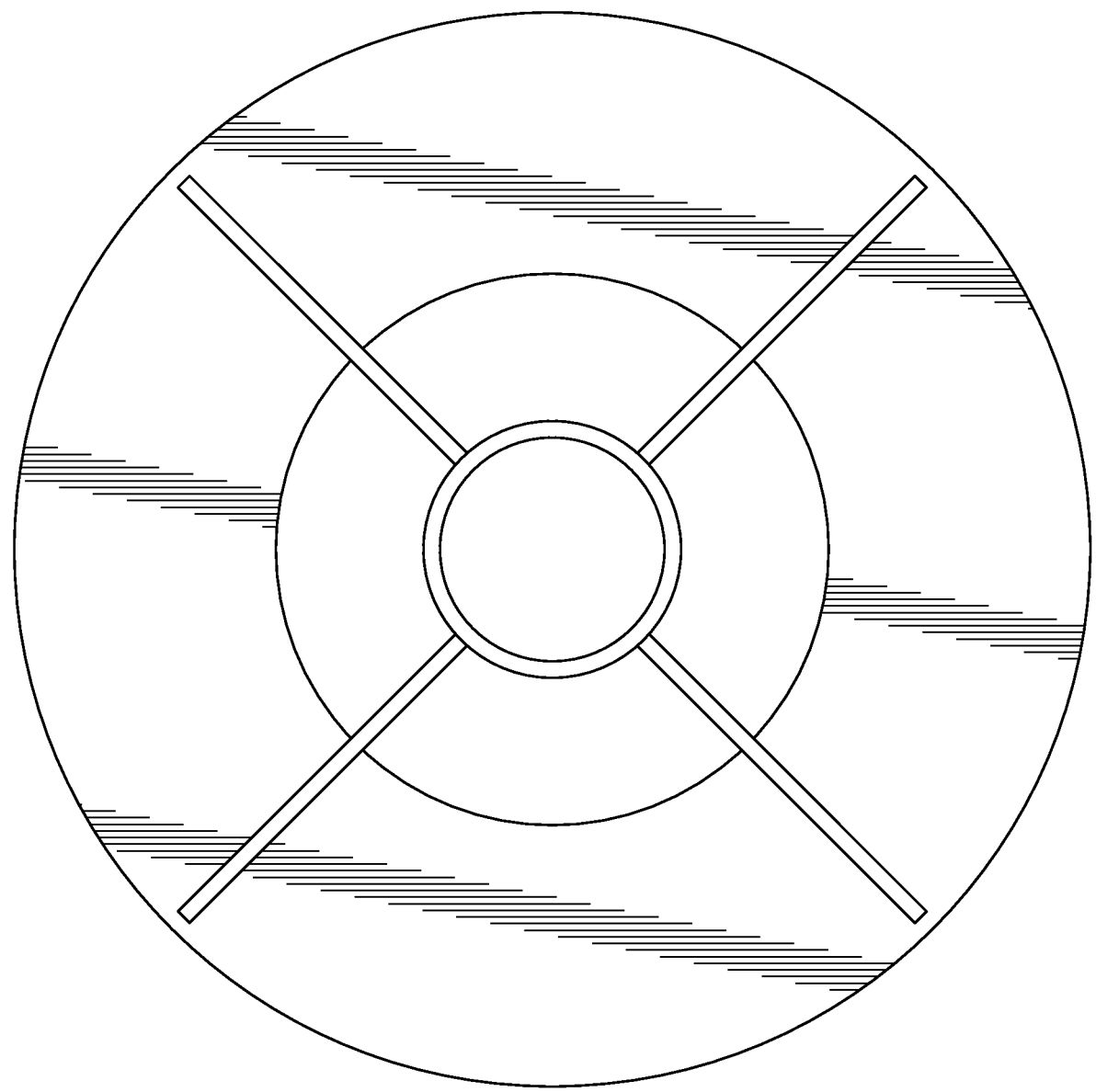
FIG. 16 is a bottom view of the support platform of FIG. 13 in a first configuration.

As illustrated in FIGS. 1 and 13, a handle or grip 14 may be arranged on the pole 6 in spaced relation between the base 2 and the inverted polyhedron structure 8. Preferably, the grip 14 is arranged in space relation between the support platform 12 and the pole adjustment mechanism 78. When the grip 14 is arranged on the pole 6 above the pole height adjustment mechanism 78, the grip 14 may be height adjustable. In an embodiment the grip 14 is arranged in a vertical configuration around the pole 6. Those skilled in the art, however, will appreciate that the handle or grip could be arranged in a horizontal configuration or radiate outward from the pole without deviating from the disclosure.

As illustrated in FIGS. 1 and 13, a basket 16 may be arranged on the pole 6 in spaced relation between the base 2 and the inverted polyhedron structure 8. Preferably, the basket 16 is arranged in spaced relation between the grip 14 and pole height adjustment mechanism 78. The basket may be configured for receiving at least one of a beverage, a cell phone, and other patient convenience items. Preferably, the pole 6 passes through a central axis of the basket 16. Optionally, the pole may be arranged on an outside surface of the basket.

While the preferred forms and embodiments of the IV fluid bag support assembly have been illustrated and described, it will be apparent to those of ordinary skill in the art that various changes and modifications may be made without deviating from the novel concepts thereof.

What is claimed is:

1. An intravenous fluid bag supporting assembly comprising:
    (a) a mobile base including a plurality of wheels;
    (b) a telescoping pole having a lower end connected with said base and having a longitudinal axis; and
    (c) a polyhedron structure connected with an upper end of said pole and configured to receive at least one intravenous fluid bag, said telescoping pole longitudinal axis extending through a portion of said polyhedron structure, a first portion of said polyhedron structure including a first pair of adjacent side wall surfaces having at least two hooks on each surface or at least two hangers on each surface, said polyhedron structure first portion having a perimeter defining a first horizontal cross section of said polyhedron structure, a second portion of said polyhedron structure including a second pair of adjacent side wall surfaces each having at least two hooks on each surface or at least two hangers on each surface, said polyhedron structure second portion having a perimeter defining a second horizontal cross section of said polyhedron structure that is less than the perimeter of said polyhedron structure first portion.

2. The assembly according to claim 1, wherein at least one side wall surface of said first and second pair of adjacent side wall surfaces includes indicia, said telescoping pole longitudinal axis extending through a central portion of said polyhedron structure first and second portions, said polyhedron structure first portion being arranged above said polyhedron structure second portion.

3. The assembly according to claim 2, wherein:
    (a) said indicia is at least one of a color, number and icon; and
    (b) said first pair of adjacent sidewall surfaces having at least two hooks or at least two hangers has said at least two hooks on each surface and said second pair of adjacent sidewall surfaces having at least two hooks or at least two hangers has said at least two hangers on each surface.

4. The assembly according to claim 2, wherein said polyhedron structure further includes a third portion arranged between said first and second portions, said third portion having a progressively decreasing width in a direction from said first portion to said second portion.

5. The assembly according to claim 1, and further comprising a light assembly arranged on said pole in spaced relation between said polyhedron structure and said base.

6. The assembly according to claim 5, wherein said light assembly comprises
   (a) a platform containing a central through opening for receiving said pole and receiving a plurality of intravenous fluid lines; and
   (b) a plurality of lights connected with a perimeter of said light assembly platform.

7. The assembly according to claim 6, wherein said light assembly platform has a perimeter shape in cross-section corresponding with a perimeter shape in cross-section of said polyhedron structure.

8. The assembly according to claim 6, wherein the number of lights corresponds to the number of side surfaces of said polyhedron structure.

9. The assembly according to claim 5, and further comprising a support platform containing a central through opening for receiving said pole and receiving a plurality of intravenous fluid lines.

10. The assembly according to claim 9, wherein said support platform is arranged on said pole in spaced relation between said light assembly and said base.

11. The assembly according to claim 9, and further comprising a plurality of housings, an amount of said plurality of housings being equal to an amount of side surfaces of said polyhedron structure first portion.

12. The assembly according to claim 11, wherein said housings and side surfaces of said polyhedron structure first portion include indicia.

13. The assembly according to claim 11, and further comprising a plurality of slots arranged around a perimeter of said support platform and configured for receiving and anchoring a capped intravenous fluid line.

14. The assembly according to claim 1, and further comprising a height adjustable hand grip arranged on said pole in spaced relation between said polyhedron structure and said base.

15. The assembly according to claim 1, and further comprising a storage basket arranged on said pole in spaced relation between said polyhedron structure and said base.

16. The assembly according to claim 1, wherein said base has a mass greater than a mass of said polyhedron structure.

17. An intravenous fluid bag supporting assembly comprising:
   (a) a mobile base including a plurality of wheels;
   (b) a telescoping pole having a lower end connected with said base and having a longitudinal axis; and
   (c) a polyhedron structure connected with an upper end of said pole and configured to receive at least one intravenous fluid bag, said telescoping pole longitudinal axis extending through a portion of said polyhedron structure, a first portion of said polyhedron structure having a perimeter, a second portion of said polyhedron structure having a perimeter that is less than the perimeter of said polyhedron structure first portion, said first portion being arranged above said second portion, wherein at least one of said first portion or said second portion includes a pair of adjacent side wall surfaces having at least one hook on each surface or at least one hanger on each surface.

18. The assembly according to claim 17, wherein said pair of adjacent side wall surfaces includes indicia, said telescoping pole longitudinal axis extending through a central portion of said polyhedron structure first and second portions.

* * * * *